(12) United States Patent
Williams et al.

(10) Patent No.: US 8,507,745 B1
(45) Date of Patent: Aug. 13, 2013

(54) PROCESSES AND SYSTEMS FOR TREATING AROMATIC FEED INCLUDING AN AROMATIC COMPONENT AND NITROGEN-CONTAINING IMPURITIES, AND PROCESSES AND SYSTEMS FOR PREPARING A REACTION PRODUCT OF THE AROMATIC COMPONENT

(75) Inventors: Chad A. Williams, Des Plaines, IL (US); Wugeng Liang, Elgin, IL (US); Patrick Jerome Bullen, Elmhurst, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 13/402,371

(22) Filed: Feb. 22, 2012

(51) Int. Cl.
*C07C 7/12* (2006.01)

(52) U.S. Cl.
USPC .................. 585/807; 585/823; 208/254 R

(58) Field of Classification Search
None
See application file for complete search history.

(56) References Cited

U.S. PATENT DOCUMENTS

| | | | |
|---|---|---|---|
| 3,193,496 A * | 7/1965 | Hartung | 208/212 |
| 4,229,587 A | 10/1980 | Murib | |
| 5,091,586 A | 2/1992 | Higuchi et al. | |
| 5,942,650 A | 8/1999 | Gajda | |
| 7,205,448 B2 | 4/2007 | Gajda et al. | |
| 7,744,828 B2 | 6/2010 | Schmidt et al. | |
| 2011/0073527 A1 | 3/2011 | Jan et al. | |

FOREIGN PATENT DOCUMENTS

| WO | 0035836 A1 | 6/2000 |
|---|---|---|
| WO | 0107383 A1 | 2/2001 |

OTHER PUBLICATIONS

Ogunsola, O.M., "Removal of Nitrogen from Liquid Fuels by Supercritical Fluid," Ultraclean Transportation Fuels: ACS Symposium Series, vol. 959, Chapter 12, pp. 155-168, 2007.

* cited by examiner

*Primary Examiner* — Tam M Nguyen
(74) *Attorney, Agent, or Firm* — Mark R Willis

(57) ABSTRACT

Processes and systems for treating an aromatic feed comprising an aromatic component and nitrogen-containing impurities, as well as processes and systems for preparing a reaction product of an aromatic component from an aromatic feed comprising the aromatic component and nitrogen-containing impurities, are provided herein. In an embodiment, a process for treating an aromatic feed comprising an aromatic component and nitrogen-containing impurities includes adsorbing a portion of the nitrogen-containing impurities from the aromatic feed to produce a treated aromatic feed comprising the aromatic component and residual nitrogen-containing impurities. The treated aromatic feed and water are mixed to produce a hydrated aromatic feed. A purified aromatic feed and a water component are distilled from the hydrated aromatic feed in a distillation stage, wherein the water component comprises residual nitrogen-containing impurities from the treated aromatic feed and wherein the purified aromatic feed comprises the aromatic component.

11 Claims, 3 Drawing Sheets

PROCESSES AND SYSTEMS FOR TREATING AROMATIC FEED INCLUDING AN AROMATIC COMPONENT AND NITROGEN-CONTAINING IMPURITIES, AND PROCESSES AND SYSTEMS FOR PREPARING A REACTION PRODUCT OF THE AROMATIC COMPONENT

TECHNICAL FIELD

The present invention generally relates to processes and systems for treating an aromatic feed that includes an aromatic component and nitrogen-containing impurities, as well as processes and systems for preparing a reaction product of an aromatic component from the aromatic feed. In particular, the present invention relates to processes and systems for removing nitrogen-containing impurities from the aromatic feed.

BACKGROUND

Reaction products of aromatic compounds, such as alkylated aromatic compounds, are common petrochemical products that are useful as intermediates for the preparation of other widely-used industrial compounds. For example, cumene (also known in the art as isopropyl benzene) is widely used as an intermediate in the production of phenol and acetone, and ethylbenzene is widely used as an intermediate in the production of styrene.

Alkylated aromatic compounds are generally prepared by reacting aromatic compounds with olefins in the presence of an aromatic alkylation catalyst, such as phosphoric acid catalysts or recently developed zeolitic acid catalysts. Processes of and systems for producing alkylated aromatic compounds are known in the art.

Aromatic feed including aromatic compounds to be reacted often includes nitrogen-containing impurities such as indoles; pyridines; quinolones; diethanol amine (DEA); and morpholines including N-formyl-morpholine (NFM) and N-methyl-pyrrolidone (NMP). The presence of nitrogen-containing impurities in aromatic feed is generally undesirable for various reasons. For example, nitrogen-containing impurities may form deposits on aromatic alkylation catalysts during alkylation of the aromatic compounds, thereby contaminating the aromatic alkylation catalysts. Such contamination adversely affects catalyst performance and catalyst life and increases regeneration frequency of the aromatic alkylation catalysts. During regeneration, accumulated nitrogen compounds and coke are combusted from the aromatic alkylation catalysts to regenerate the catalysts. Even very low nitrogen concentrations in the aromatic feed may increase catalyst regeneration frequency due to formation of deposits from the nitrogen-containing impurities on the aromatic alkylation catalysts.

Techniques have been sought to address the impact of nitrogen-containing impurities from aromatic feed on the aromatic alkylation catalysts. For example, techniques have been developed for treating the aromatic alkylation catalysts themselves, such as through desorption of the impurities from the aromatic alkylation catalysts after contamination thereof. As another example, adsorption techniques have been developed, using guard bed systems, for adsorbing nitrogen-containing impurities from aromatic feed prior to alkylation in the presence of the aromatic alkylation catalyst. In the guard bed systems, the aromatic feed is passed over a fixed bed of adsorbent material that is capable of chemically adsorbing the nitrogen-containing impurities from the aromatic feed. However, existing guard bed systems are generally incapable of adsorbing all nitrogen-containing impurities from the aromatic feed. As a result, residual nitrogen-containing impurities generally remain in the treated aromatic feed after passing through the guard bed systems. Simply increasing capacity of the guard bed systems is an undesirable and often imperfect approach to removing greater amounts of nitrogen-containing impurities from the aromatic feed due to the nitrogen-containing impurities in the aromatic feed having different degrees of basicity with some of the nitrogen-containing impurities having basicity that falls outside of an operating range of the guard bed systems.

Accordingly, it is desirable to provide processes and systems that are configured to assist with removal of residual nitrogen-containing impurities from aromatic feed after adsorption of a portion of the nitrogen-containing impurities from the aromatic feed. In addition, it is desirable to remove the residual nitrogen-containing impurities from the aromatic feed without increasing capacity of the guard bed systems. Furthermore, other desirable features and characteristics of the present invention will become apparent from the subsequent detailed description of the invention and the appended claims, taken in conjunction with the accompanying drawings and this background of the invention.

BRIEF SUMMARY

Processes and systems for treating an aromatic feed comprising an aromatic component and nitrogen-containing impurities, as well as processes and systems for preparing a reaction product of an aromatic component from an aromatic feed comprising the aromatic component and nitrogen-containing impurities, are provided herein. In an embodiment, a process for treating an aromatic feed comprising an aromatic component and nitrogen-containing impurities includes adsorbing a portion of the nitrogen-containing impurities from the aromatic feed to produce a treated aromatic feed comprising the aromatic component and residual nitrogen-containing impurities. The treated aromatic feed and water are mixed to produce a hydrated aromatic feed. A purified aromatic feed and a water component are distilled from the hydrated aromatic feed, wherein the water component comprises residual nitrogen-containing impurities from the treated aromatic feed and wherein the purified aromatic feed comprises the aromatic component.

In another embodiment, a process for preparing a reaction product of an aromatic component from an aromatic feed comprising the aromatic component and nitrogen-containing impurities includes adsorbing a portion of the nitrogen-containing impurities from the aromatic feed to produce a treated aromatic feed comprising the aromatic component and residual nitrogen-containing impurities. The treated aromatic feed and water are mixed to produce a hydrated aromatic feed. A purified aromatic feed and a water component are distilled from the hydrated aromatic feed in a distillation stage, wherein the water component comprises residual nitrogen-containing impurities from the treated aromatic feed and wherein the purified aromatic feed comprises the aromatic component. The purified aromatic feed is reacted in a reaction stage to produce a reactor effluent comprising the reaction product of the aromatic component and an unreacted aromatic component.

In another embodiment, a system for treating an aromatic feed comprising an aromatic component and nitrogen-containing impurities includes an adsorption stage for receiving the aromatic feed and for adsorbing a portion of the nitrogen-containing impurities from the aromatic feed to produce a treated aromatic feed comprising the aromatic component and residual nitrogen-containing impurities. A water input is downstream of the adsorption stage for mixing the treated aromatic feed and water to form a hydrated aromatic feed. A distillation stage is in fluid communication with the adsorption stage, with the water input in fluid communication with the distillation stage or upstream thereof, for distilling a purified aromatic feed and a water component from the hydrated aromatic feed. The water component comprises residual nitrogen-containing impurities from the treated aromatic feed and the purified aromatic feed comprises the aromatic component.

BRIEF DESCRIPTION OF THE DRAWINGS

The present invention will hereinafter be described in conjunction with the following drawing figures, wherein like numerals denote like elements, and wherein.

DETAILED DESCRIPTION

The following detailed description is merely exemplary in nature and is not intended to limit the invention or the application and uses of the invention. Furthermore, there is no intention to be bound by any theory presented in the preceding background or the following detailed description.

Figure 1:
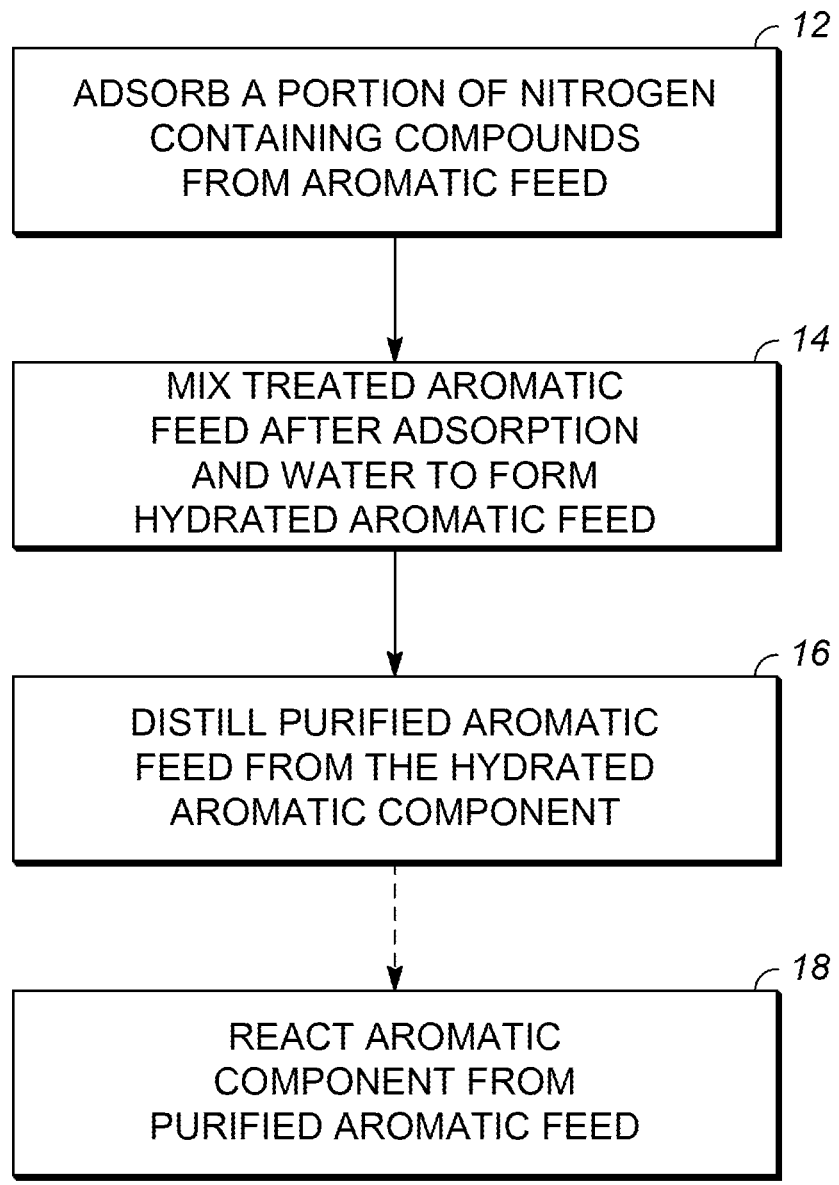
FIG. 1 is a process flow chart illustrating a process for treating an aromatic feed and preparing a reaction product in accordance with an exemplary embodiment.

Processes and systems for treating an aromatic feed that includes an aromatic component and nitrogen-containing impurities, as well as processes and systems for preparing a reaction product of an aromatic component from the aromatic feed, are provided herein. Referring to FIG. 1, the processes employ adsorption (STEP 12) to remove a portion of the nitrogen-containing impurities from the aromatic feed, followed by mixing (STEP 14) the resulting treated aromatic feed with water to produce a hydrated aromatic feed and distilling (STEP 16) a purified aromatic feed from the hydrated aromatic feed. Residual nitrogen-containing impurities are included in the water component that is distilled from the hydrated aromatic feed in STEP 16 and, thus, are separated from the purified aromatic feed. By mixing the treated aromatic feed and water in STEP 14 followed by distilling in STEP 16, residual nitrogen-containing impurities can be removed from the treated aromatic feed after adsorption in STEP 12, thereby enhancing removal of the nitrogen-containing impurities from the aromatic feed over processes that only employ adsorption. Mixing the treated aromatic feed and water in STEP 14, followed by distilling in STEP 16, can reduce adsorption requirements in STEP 12 and enable life of adsorbent materials employed in adsorption (STEP 12) to be maximized while removing the same or more amounts of nitrogen-containing impurities from the aromatic feed than can be achieved by adsorption (STEP 12) alone. Although the purified aromatic feed can be employed for any purpose, the purified aromatic feed may be particularly useful as a reactant stream for forming reaction products of the aromatic component (STEP 18), such as alkylated aromatic compounds, due to the aforementioned removal of nitrogen-containing impurities.

Aromatic feed, as referred to herein, is the feed that is subject to adsorption (STEP 12, FIG. 1) and includes at least some fresh feed of one or more aromatic compounds that has not been previously treated for removal of nitrogen-containing impurities. The aromatic component that is included in the aromatic feed is not particularly limited and can include one or more aromatic compounds that are useful in downstream reactions, such as alkylation reactions, for preparing reaction products of the aromatic compounds. For example, the one or more aromatic compounds may be chosen from, but are not limited to, benzene, naphthalene, anthracene, phenanthrene, substituted derivatives thereof, and combinations thereof. In one specific example, the aromatic component includes benzene. The aromatic component may be present in the aromatic feed in an amount of from about 5 to 99.9 percent by weight (wt %), such as from about 80 to 99.9 wt %, for example from about 98 to about 99.9 wt %, based on the total amount of all components present in the aromatic feed. Nitrogen-containing impurities that may be present in the aromatic feed include, but are not limited to, indoles; pyridines; quinolones; diethanol amine (DEA); and morpholines including N-formyl-morpholine (NFM) and N-methyl-pyrrolidone (NMP). The nitrogen-containing impurities may be present in the aromatic feed in an amount of from about 1 to about 10,000 parts per billion by weight (wt ppb), such as from about 30 to about 1000 wt ppb, based on the total weight of all components present in the aromatic feed. The balance of the aromatic feed may optionally include hydrocarbons other than aromatic compounds, trace amounts of water (so long as any water is not present in amounts that exceed specifications for adsorbent materials employed during adsorption), and/or other non-hydrocarbon impurities such as sulfur-containing impurities.

In an embodiment, and as shown in FIG. 1, a process for treating the aromatic feed including the aromatic component and the nitrogen-containing impurities includes adsorbing as described above (STEP 12, FIG. 1). The treated aromatic feed, after adsorption (STEP 12, FIG. 1), contains residual nitrogen-containing impurities due to incomplete removal of all nitrogen-containing impurities from the aromatic feed through an adsorption bed (STEP 12). Such residual nitrogen-containing impurities may be present in the treated aromatic feed due to the residual nitrogen-containing impurities having basicity that falls outside of an operating range within which adsorption (STEP 12) can remove such impurities, or due to less extensive adsorption bed usage than may otherwise be required to completely remove all nitrogen-containing impurities from the aromatic feed. In an embodiment, the treated aromatic feed includes residual nitrogen-containing impurities in an amount of from about 1 to about 5000 wt ppb, such as from about 30 to about 100 wt ppb, based upon the total weight of all components present in the treated aromatic feed.

After adsorption (STEP 12, FIG. 1), the treated aromatic feed and water are mixed (STEP 14) to produce a hydrated aromatic feed, which is then subject to distilling (STEP 16). By mixing the treated aromatic feed and water in STEP 14, residual nitrogen-containing impurities diffuse into the water and are subsequently distilled with the water in STEP 16, thereby resulting in purified aromatic feed that has less residual nitrogen-containing impurities than the treated aromatic feed after adsorption alone in STEP 12. In an embodiment, the treated aromatic feed and water are mixed in STEP 14 directly after adsorption in STEP 12, i.e., in the absence of intervening steps between adsorption (STEP 12) and mixing (STEP 14) of the treated aromatic feed and water. For example, the treated aromatic feed and water may be mixed in liquid form prior to distilling in STEP 16, thereby forming the hydrated aromatic feed, followed by distilling the hydrated aromatic feed in STEP 16. In another embodiment, the treated aromatic feed and water are mixed during distilling such that mixing (STEP 14) and distilling (STEP 16) may occur concurrently.

To provide sufficient amounts of water for removing the residual nitrogen-containing impurities from the treated aromatic feed during distilling (STEP 16), the treated aromatic feed and water may be mixed with water present in an amount of from about 10 to about 10,000 parts per million by weight (wt ppm), such as from about 200 to about 500 wt ppm, based upon the total weight of the combined aromatic feed and water. With such amounts of water mixed with the treated aromatic feed in STEP 14, a desirable hydration level of the hydrated aromatic feed during distilling (STEP 16) may be established to ensure that the residual nitrogen-containing impurities can be distilled with the water from the hydrated aromatic feed in STEP 16.

During or after mixing the treated aromatic feed and water in STEP 14, and as shown in FIG. 1, a purified aromatic feed and a water component may be distilled from the hydrated aromatic feed in a distillation stage (STEP 16). During distilling of the purified aromatic feed and the water component from the hydrated aromatic feed in STEP 16, water is generally vaporized to form the water component and is ultimately separated as an overhead stream. The water component that is distilled from the hydrated aromatic feed in STEP 16 includes residual nitrogen-containing impurities from the treated aromatic feed. The purified aromatic feed represents a portion of the treated aromatic feed that is collected in liquid form. In this regard, the purified aromatic feed includes the aromatic component after distillation. Additionally, the purified aromatic feed may be substantially free of water after distilling, e.g., the purified aromatic feed may have water present in an amount of less than about 200 wt ppm water, such as less than about 50 wt ppm water or less than about 10 wt ppm water, which amounts may be sufficiently low to avoid deleterious effects on catalysts that are employed in an optional downstream reaction step (STEP 18) that may receive the purified aromatic feed as described below.

In an embodiment, as alluded to above and as shown in FIG. 1, the process may further include reacting the purified aromatic feed to produce a reaction product of the aromatic component in STEP 18. The purified aromatic feed may be reacted in any known reaction in which an aromatic compound is a reactant, with the aromatic compound optionally reacted with another reactant. In an embodiment, the step of reacting the purified aromatic feed (STEP 18) is further defined as alkylating the aromatic component from the purified aromatic feed through reaction with an alkylating agent, and the reaction product of the aromatic component is further defined as an alkylated aromatic component. The alkylated aromatic component may include one or more alkylated aromatic compounds. The aromatic component in the purified aromatic feed and the alkylation agent may be reacted to form the alkylated aromatic component through processes that are known in the art. For example, in alkylation processes, the alkylating agent may be an olefin and the aromatic component may be selectively alkylated with the olefin in the presence of an acidic aromatic alkylation catalyst under at least partially liquid phase conditions. The particular conditions under which the alkylation reaction is conducted depends upon the aromatic component and the olefin used. Suitable olefins that may be employed for alkylating the aromatic component include, but are not limited to, those containing from about 2 to about 20 carbon atoms. As specific examples, ethylene can be employed to alkylate benzene to form ethylbenzene, and propylene can be employed to alkylate benzene to form cumene.

A wide variety of aromatic alkylation catalysts can be used in the alkylation processes. Particularly suitable aromatic alkylation catalysts include those that may be impacted by the presence of nitrogen-containing impurities in the aromatic feed in view of the fact that such catalysts may benefit from the processes and systems described herein. One example of a suitable aromatic alkylation catalyst that may benefit from the processes and systems described herein is a zeolitic catalyst, which may be used in combination with a refractory inorganic oxide binder such as alumina or silica. Suitable zeolitic catalysts include zeolite beta, ZSM-5, PSH-3, MCM-22, MCM-36, MCM-49, and MCM-56. Such zeolitic catalysts are known in the art.

Figure 2:
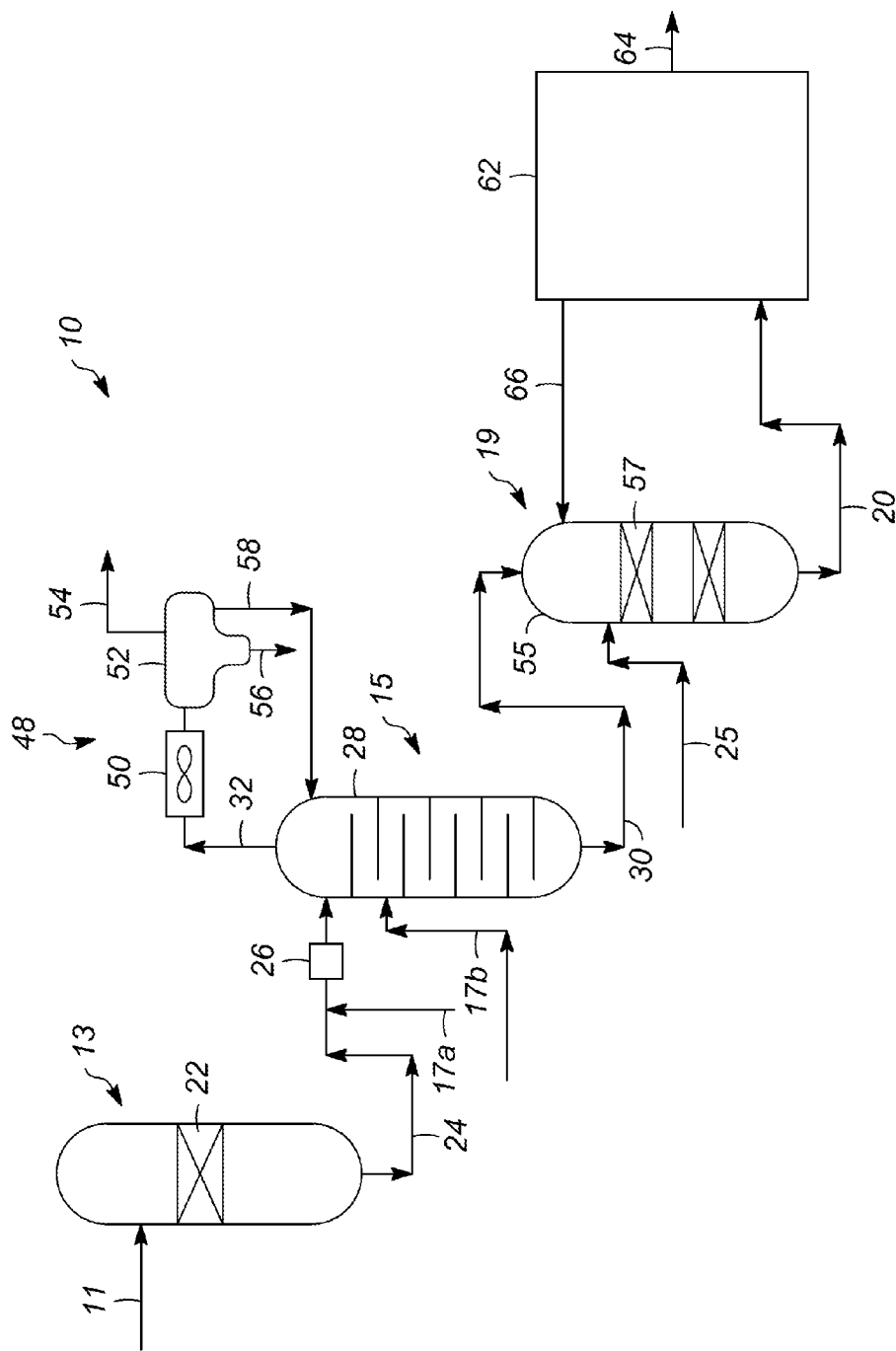
FIG. 2 is a schematic diagram of an exemplary embodiment of a system for treating an aromatic feed, as well for preparing a reaction product of an aromatic component from the aromatic feed, in accordance with the process flow shown in FIG. 1.
Figure 3:
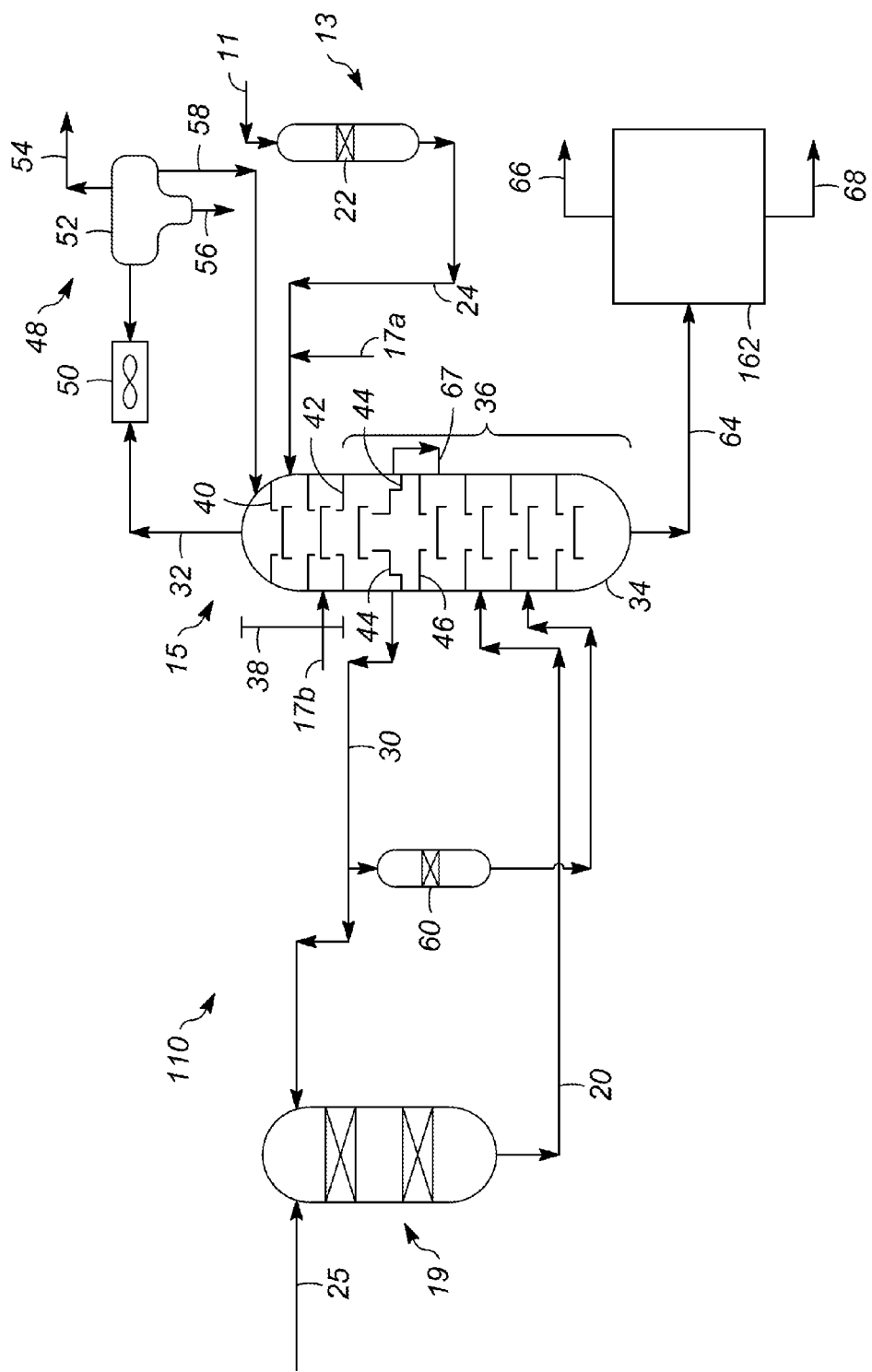
FIG. 3 is a schematic diagram of another exemplary embodiment of a system for treating an aromatic feed, as well for preparing a reaction product of an aromatic component from the aromatic feed, in accordance with the process flow shown in FIG. 1.

Exemplary embodiments of systems 10, 110 for treating aromatic feed 11, as well as for preparing a reaction product of an aromatic component from the aromatic feed, are shown in FIGS. 2 and 3. FIGS. 2 and 3 illustrate different embodiments for configuration of the systems 10, 110 that may be employed for treating aromatic feed 11 in accordance with the processes described herein. Although FIGS. 2 and 3 separately illustrate various embodiments of configurations for the adsorption stage 13, distillation stage 15, and water inputs 17a, 17b, it is to be appreciated that an exemplary system (not shown) may include both embodiments of configurations as shown in FIGS. 2 and 3.

Exemplary processes will now be described with respect to an exemplary embodiment of the system 10 as shown in FIG. 2. In this embodiment, the adsorption stage 13, the distillation stage 15, and water input 17a, 17b may be disposed upstream of a reaction stage 19. Adsorption (STEP 12, FIG. 1) can be conducted in the adsorption stage 13, with the adsorption stage 13 receiving the aromatic feed 11 and chemically adsorbing the portion of the nitrogen-containing impurities from the aromatic feed 11 to produce the treated aromatic feed 24. The adsorption stage 13 may include one or more adsorption beds 22. The adsorption beds 22, also known as guard beds, are generally fixed beds that include an adsorbent material. To adsorb the portion of the nitrogen-containing impurities from the aromatic feed 11, the aromatic feed 11 is passed over the one or more adsorption beds 22 of adsorbent material, which chemically adsorb the portion of the nitrogen-containing impurities from the aromatic feed 11. The adsorbent material can include a molecular sieve material, such as a zeolite, and can also include at least one binder. Suitable binders include, but are not limited to, clay materials. The adsorbent material may either be regenerated or discarded once spent. Such adsorption beds are well known in the art.

FIG. 2 shows water inputs 17a, 17b through which the water can be introduced and mixed (STEP 14, FIG. 1) with the treated aromatic feed 24 after adsorption. In one embodiment, the system 10 may include the water input 17a downstream of the adsorption stage 13 for mixing the treated aromatic feed 24 and water from the water input 17a to form the hydrated aromatic feed. In this embodiment, the distillation stage 15 is in fluid communication with the adsorption stage 13, with the water input 17a upstream of the distillation stage 15. The treated aromatic feed 24 and water from the water input 17a may be mixed by the convergence of the treated aromatic feed 24 and water from the water input 17a, or may be mixed by passing the hydrated aromatic feed through a mixer 26, such as a static mixer of the system 10, to effectuate uniform mixing and intimate contact between the water from the water input 17a and residual nitrogen-containing impurities and to promote diffusion of the residual nitrogen-containing impurities from the treated aromatic feed 24 to the water.

In another embodiment, the treated aromatic feed 24 and water are mixed (STEP 14, FIG. 1) in the distillation stage 15. In this embodiment, the water can be in liquid or vapor form and can be introduced separate from the treated aromatic feed 24 into the distillation stage 15. For example, in this embodiment and as shown in FIG. 2, the system 10 includes the water input 17b, which may be in fluid communication with the distillation stage 15 for mixing the treated aromatic feed 24 and water to form the hydrated aromatic feed. When the water is in vapor form, the water vapor is mixed with the treated aromatic feed 24 below an input of the treated aromatic feed 24 in the distillation stage 15. When water vapor from the water input 17b is mixed with the treated aromatic feed 24, the water vapor and treated aromatic feed 24 mix as the water vapor travels upward and the treated aromatic feed 24 travels downward during distillation. In this manner, residual nitrogen-containing impurities in the treated aromatic feed 24 may diffuse from the treated aromatic feed 24 into to the water vapor.

In the embodiment shown in FIG. 2, the distillation stage 15 may include one or more stripping columns 28 for distilling (STEP 16, FIG. 1) the purified aromatic feed 30 from the hydrated aromatic feed. The one or more stripping columns 28 are downstream of the adsorption stage 13 and upstream of any reaction stage 19 in which the aromatic compounds are reacted (STEP 18, FIG. 1), optionally with other reactants 25, to form a reaction product. In this embodiment, the purified aromatic feed 30 may be fed to the later reaction stage 19 where the aromatic component present therein may be reacted (STEP 18, FIG. 1) to form reaction products.

Although the purified aromatic feed 30 and the water component 32 are distilled from the hydrated aromatic feed, the water component 32 may include an entrained aromatic component therewith after distillation. In an embodiment, and as shown in FIG. 2, the entrained aromatic component 58 and condensed water 56 are separated from the water component 32, with the entrained aromatic component 58 recycled to the distillation stage 15. For example, as shown in FIG. 2, the water component 32 may be expelled from the one or more stripping columns 28 as an overhead stream, and the distillation stage 15 of the system 10 may include an overhead condensing stage 48 for receiving the overhead stream. The overhead condensing stage 48 may include a chiller 50 and an overhead receiver 52. During operation, the chiller 50 may condense water and entrained aromatic component 58 from the overhead stream, which may be separated in the overhead receiver 52. Uncondensed gases 54 may be expelled from the overhead receiver 52, condensed water 56 including the residual nitrogen-containing impurities may be expelled for remediation, and the entrained aromatic component 58 may be recycled to the one or more stripping columns 28 as reflux. Just as the water component 32 that is distilled from the hydrated aromatic feed generally may carry the entrained aromatic component 58 therewith, separation between the entrained aromatic component 58 and condensed water 56 is often imperfect in the overhead condensing stage 48 and some water may remain in the entrained aromatic component 58 that is recycled to the distillation stage 15. As such, the entrained aromatic component 58 that is recycled to the distillation stage 15 may be introduced at even level with or above the treated aromatic feed 24 in the distillation stage 15, due to the possible presence of water in the recycled entrained aromatic component 58, to promote mixing of water and the treated aromatic feed 24 and subsequent distillation of the water component 32 therefrom.

In this embodiment, the reaction stage 19 may include one or more reactors 55 that each include one or more catalyst beds 57 including, for example, the alkylation catalyst as described above, for reacting (STEP 18, FIG. 1) the aromatic compounds from the purified aromatic feed 30. To react the aromatic compounds from the purified aromatic feed 30, the purified aromatic feed 30 is passed over the one or more catalyst beds 57, which react the aromatic compounds, optionally with the additional reactant 25 such as the alkylating agent 25 described above. The reaction product exits the reaction stage 19 in a reactor effluent 20. In this embodiment, after reaction of the aromatic component in the purified aromatic feed 30, the reactor effluent 20 may be separated in a separation stage 62 to recover reaction product 64. Although not shown, unreacted aromatic compounds 66 and undesirable by-products may optionally be returned back to the reaction stage 19.

Exemplary processes will now be described with respect to the exemplary embodiment of the system 110 as shown in FIG. 3. In this embodiment, the distillation stage 15 may be disposed downstream of the adsorption stage 13 and may be disposed in a loop with the reaction stage 19 to receive reactor effluent 20 and return an unreacted aromatic component from the reactor effluent 20 (as well as fresh aromatic feed) to the reaction stage 19.

In this embodiment, adsorption (STEP 12, FIG. 1) can be conducted in the adsorption stage 13 as described above, and the treated aromatic feed 24 and water can be mixed (STEP 14, FIG. 1) as also described in detail above. However, in this embodiment, the purified aromatic feed 30 and water component 32 are distilled (STEP 16, FIG. 1) in the presence of the reactor effluent 20 that includes the reaction product of the aromatic component (from STEP 18, FIG. 1), as well as an unreacted aromatic component. For example, the distillation stage 15 may include a common distillation column 34, and the purified aromatic feed 30, the water component 32, and the reactor effluent 20 may be distilled in the common distillation column 34, such as in a benzene recovery column 34 in an alkylated benzene process, with the distillation stage 15 disposed downstream of the adsorption stage 13 and further disposed in a loop with the reaction stage 19 to receive reactor effluent 20 and return unreacted aromatic component (as well as fresh aromatic feed) in the purified aromatic feed 30 to the reaction stage 19 for reaction, optionally with other reactants 25. The unreacted aromatic component in the reactor effluent 20 refers to any aromatic compounds or combination of aromatic compounds in the reactor effluent 20 that remain unreacted after reaction (STEP 18, FIG. 1) in the reaction stage 19. As such, in this embodiment, the purified aromatic feed 30 represents portions of the treated aromatic feed 24, as well as portions of aromatic feed that may originate from other sources such as the unreacted aromatic component, that are collected in liquid form during distillation (STEP 16, FIG. 1). In addition to the unreacted aromatic component and reaction product of the aromatic component, the reactor effluent 20 may also include additional compounds, such as by-products of reaction including polyalkylated aromatic compounds or other unreacted reactants. Although not shown, it is to be appreciated that such additional compounds may be separated from the reactor effluent 20 prior to the distillation stage 15 in this embodiment. Alternatively, as shown in FIG. 3, the by-products such as polyalkylated aromatic compounds may be included in the purified aromatic feed 30, and a portion of the purified aromatic feed 30 may be directed through a transalkylation reactor 60 to convert the polyalkylated aromatic compounds to desirable mono-alkylated aromatic compounds. Use of transalkylation reactors in alkylation processes is well known to those of skill in the art, and such transalkylation reactors can also be employed in the embodiment of the system 10 as shown in FIG. 2 (although not shown).

In the embodiment shown in FIG. 3, the common distillation column 34 in distillation stage 15 may have separate sections 36, 38 including a first section 36 primarily for distilling the unreacted aromatic component from reaction products, such as alkylated aromatic compounds, in the reactor effluent 20 and a second section 38, located above the first section 36, for distilling the purified aromatic feed 30 and the water component 32 from the hydrated aromatic feed. The reactor effluent 20 may be introduced into the first section 36 of the common distillation column 34, and the treated aromatic feed 24 may be introduced into the second section 38. In an embodiment, the treated aromatic feed 24 and water are mixed (STEP 14, FIG. 1) in the presence of the reactor effluent 20. For example, the treated aromatic feed 24 may be introduced into the second section 38 of the common distillation column 34 as such, i.e., without first mixing the treated aromatic feed 24 and water. In this embodiment, the water (either in liquid or vapor form) and the treated aromatic feed 24 are separately introduced into the second section 38 of the common distillation column 34. For example, the water vapor may be introduced through the water input 17*b*. Alternatively, the treated aromatic feed 24 may be introduced into the second section 38 as the hydrated aromatic feed, with the treated aromatic feed 24 and water having been mixed (STEP 14, FIG. 1) prior to introduction into the second section 38 for distilling (STEP 16, FIG. 1). For example, the water may be introduced through the water input 17*a*.

In the embodiment shown in FIG. 3, the reactor effluent 20, the purified aromatic feed 30, and the water component 32 may be in direct vapor communication during the distillation (STEP 16, FIG. 1). Further, direct liquid flow is hindered between the reactor effluent 20 and the purified aromatic feed 30, such as through configuration of the first section 36 and the second section 38 as described below. Of course, the water component 32 is in vapor form during distillation such that liquid flow of the water component 32 during distillation is immaterial. As shown in FIG. 3, the second section 38 of the column 34 may include one or more fractionation plates 40 and a tray 42 at the bottom of the second section 38 for catching and retaining liquid in the second section 38. During distillation (STEP 16, FIG. 1) of the purified aromatic feed 30 and the water component 32 from the hydrated aromatic feed, water is generally vaporized and is ultimately expelled from the column 34 in the water component 32 as an overhead stream. The aromatic compounds from the treated aromatic feed 24 predominantly remain in liquid form (or are condensed if in vapor form) and are collected in the tray 42. Additionally, the unreacted aromatic component from the reactor effluent 20, when in vapor form, may travel upwards and into the second section 38, where the unreacted aromatic component is condensed and collected with the aromatic compounds from the treated aromatic feed 24 to form the purified aromatic feed 30 in the tray 42 of the second section 38. By collecting the purified aromatic feed 30 in the tray 42, as opposed to allowing the purified aromatic feed 30 to flow directly into the first section 36 (as would occur in the absence of the tray 42), direct liquid flow is hindered between the reactor effluent 20 in the first section 36 and the purified aromatic feed 30. The purified aromatic feed 30 collected in the tray 42 may be expelled directly from the column 34. Alternatively, the purified aromatic feed 30 collected in the tray 42 of the second section 38 may overflow the tray 42 and collect in an underlying tray 44 within the first section 36. The underlying tray 44 may be in liquid isolation from reaction products, such as alkylated aromatic compounds, that are distilled from the reactor effluent 20 (although a reflux line 67 may be selectively controlled to return contents of the underlying tray 44 to lower plates 46 in the first section 36 that contains the reactor effluent 20 and/or reaction products). The purified aromatic feed 30 in the underlying tray 44 may then be expelled from the column 34. In this manner, to the extent that water may still be present in the purified aromatic feed 30 that is present in the tray 42 of the second section 38, retention of the purified aromatic feed 30 in the tray 42 in the second section 38 may provide additional opportunity for separation of the water from the purified aromatic feed 30 before the purified aromatic feed 30 is removed from the distillation stage 15 or mixed with unreacted aromatic compounds in the underlying tray 44 (which are substantially isolated from any water that is introduced into the column 34 by virtue of the use of the tray 42). In this manner, water contamination of the reaction product, such as alkylated aromatic compounds, can be minimized or avoided. Separated reaction product 64 from the column 34 may be further separated in a downstream separation stage 162 to separate unreacted aromatic compounds 66 and undesirable by-products from desirable reaction product 68. Such separation stages are well known in the art.

In the embodiment shown in FIG. 3, the entrained aromatic component 58 and condensed water 56 may be separated from the water component 32, with the entrained aromatic component 58 recycled to the distillation stage 15, in the same manner as described above for the embodiment shown in FIG. 2. Likewise, the purified aromatic feed 30 can be fed to the reaction stage 19 and reacted (STEP 18, FIG. 1) in the same manner as described above for the embodiment shown in FIG. 2.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A process for treating an aromatic feed comprising an aromatic component and nitrogen-containing impurities, said process comprising the steps of:

adsorbing a portion of the nitrogen-containing impurities from the aromatic feed to produce a treated aromatic feed comprising the aromatic component and residual nitrogen-containing impurities;

mixing the treated aromatic feed and water to produce a hydrated aromatic feed;

distilling a purified aromatic feed and a water component from the hydrated aromatic feed, wherein the water component comprises residual nitrogen-containing impurities from the treated aromatic feed and wherein the purified aromatic feed comprises the aromatic component.

2. The process of claim 1, wherein the treated aromatic feed and water are mixed in liquid form prior to distilling.

3. The process of claim 1, wherein the treated aromatic feed and water are mixed during distilling.

4. The process of claim 1, wherein the treated aromatic feed and water are mixed with water present in an amount of from about 10 to about 10,000 parts per million by weight based upon the total weight of the combined treated aromatic feed and water.

5. The process of claim 1, wherein the purified aromatic feed and the water component are distilled in the presence of a reactor effluent comprising a reaction product of the aromatic component and an unreacted aromatic component.

6. The process of claim 5, wherein the treated aromatic feed and water are mixed in the presence of the reactor effluent.

7. The process of claim 5, wherein the reactor effluent, the purified aromatic feed, and the water component are in direct vapor communication during distilling and wherein direct liquid flow is hindered between the reactor effluent and the purified aromatic feed.

8. The process of claim 1, wherein the water component distilled from the hydrated aromatic feed comprises entrained aromatic component, and wherein the entrained aromatic component and water are separated from the water component with the entrained aromatic component recycled and introduced during distilling.

9. The process of claim 1, wherein the purified aromatic component is substantially free of water after distilling.

10. The process of claim 1, wherein the step of adsorbing the portion of the nitrogen-containing impurities produces the treated aromatic feed including residual nitrogen-containing impurities in an amount of from about 1 to about 5000 parts per billion by weight based upon the total weight of all components present in the treated aromatic feed.

11. The process of claim 1, wherein the portion of the nitrogen-containing impurities is adsorbed from the aromatic feed comprising the aromatic component including an aromatic compound chosen from benzene, naphthalene, anthracene, phenanthrene, substituted derivatives thereof, and combinations thereof.

\* \* \* \* \*